United States Patent
Zapp et al.

(10) Patent No.: US 6,723,368 B1
(45) Date of Patent: Apr. 20, 2004

(54) METHOD FOR ENHANCING POST-PROCESSING CONTENT OF BENEFICIAL COMPOUNDS IN BEVERAGES NATURALLY CONTAINING SAME

(76) Inventors: Loretta M. Zapp, c/o Oncology Sciences Corporation, 1120 Capital of Texas Highway South, Building Three, Suite 205, Austin, TX (US) 78746; Thomas J. Slaga, c/o AMC Cancer Research Center, 1600 Pierce St., Denver, CO (US) 80214; Jifu Zhao, c/o AMC Cancer Research Center, 1600 Pierce St., Denver, CO (US) 80214; Mark Lang, 4822 Mandavilla Way, Apex, NC (US) 27502

( * ) Notice: Subject to any disclaimer, the term of this patent is extended or adjusted under 35 U.S.C. 154(b) by 221 days.

(21) Appl. No.: 10/001,928

(22) Filed: Oct. 31, 2001

Related U.S. Application Data

(63) Continuation-in-part of application No. 09/843,543, filed on Apr. 25, 2001, now abandoned, which is a continuation-in-part of application No. 09/481,279, filed on Jan. 11, 2000, now abandoned, which is a continuation-in-part of application No. 09/468,560, filed on Dec. 21, 1999, now abandoned.

(51) Int. Cl.$^7$ ................. A23F 5/00; A23F 5/16
(52) U.S. Cl. ............. 426/594; 426/597; 426/431; 426/432; 426/435
(58) Field of Search ................. 426/594, 432, 426/590, 593, 597, 598, 431, 435

(56) References Cited

U.S. PATENT DOCUMENTS

| | | |
|---|---|---|
| 3,114,641 A | 12/1963 | Sparti et al. |
| 3,657,424 A | 4/1972 | Akins et al. |
| 4,053,652 A | 10/1977 | Mahlmann |
| 4,156,031 A * | 5/1979 | Hamell et al. |
| 4,325,975 A | 4/1982 | Lindon et al. |
| 4,328,255 A * | 5/1982 | Roselius et al. |
| 4,497,800 A | 2/1985 | Larson et al. |
| 4,722,847 A | 2/1988 | Heckert |
| 4,737,375 A | 4/1988 | Nakel et al. |
| 4,740,380 A | 4/1988 | Melachouris et al. |
| 4,851,221 A | 7/1989 | Pak et al. |
| 4,857,351 A * | 8/1989 | Neilson et al. |
| 4,904,484 A | 2/1990 | Small et al. |
| 4,919,963 A | 4/1990 | Heckert |
| 4,985,271 A | 1/1991 | Neilson et al. |
| 5,232,709 A | 8/1993 | Saltman et al. |
| 5,716,649 A | 2/1998 | Nam |
| 6,045,843 A | 4/2000 | Gurol |
| 6,086,927 A | 7/2000 | Frielich et al. |
| 6,093,436 A * | 7/2000 | Zheng et al. |
| 6,106,874 A | 8/2000 | Liebrecht et al. |
| 6,312,753 B1 | 11/2001 | Kealey et al. |

FOREIGN PATENT DOCUMENTS

| | | |
|---|---|---|
| EP | 0 075 114 B1 | 6/1985 |
| EP | 1370118 | 1/1986 |

* cited by examiner

Primary Examiner—Anthony J. Weier
(74) Attorney, Agent, or Firm—David G. Henry

(57) ABSTRACT

A process for enhancing polyphenolics content of beverages brewed from polyphenolic containing, processed beverage substrate by pre-soaking substrate (coffee beans, for example) before roasting and then quenching the substrate after processing with the liquid in which the substrate was first "pre-soaked." Beverages produced from the treated substrate exhibit substantially increased polyphenolics content, when compared to conventionally processed beverage substrate of the same nature and processing.

9 Claims, No Drawings

METHOD FOR ENHANCING POST-PROCESSING CONTENT OF BENEFICIAL COMPOUNDS IN BEVERAGES NATURALLY CONTAINING SAME

CITATION TO PRIOR APPLICATION

This is a continuation-in-part with respect to U.S. application, Ser. No. 09/843,543 filed on Apr. 25, 2001 now abandoned which was a continuation-in-part of U.S. application Ser. No. 09/481,279 filed on Jan. 11, 2000 now abandoned which, in turn, was a continuation-in-part of U.S. application Ser. No. 09/468,560 filed on Dec. 21, 1999 now abandoned, from all of which priority is claimed under 35 U.S.C. §120.

BACKGROUND OF THE INVENTION

1. Field of the Invention

The present invention relates to nutritional supplements.

2. Background Information

Recent research indicates that polyphenols in fruits, vegetables, common beverages and plants possess the capacity for diversified, beneficial pharmacological activities. It is widely accepted that these compounds, recently dubbed "vitamin P", possess a wide range of beneficial pharmacological activities which include stabilizing capillary wall tissues, maintaining proper permeability and flexibility of capillaries, and preventing cardiovascular diseases. Numerous studies have also shown that most plant polyphenols possess cancer preventive capacity because of their profound antioxidant activity.

It is, of course, well-known that coffee contains caffeine. However, a lesser-known fact is that coffee contains potentially highly beneficial condensed tannin and polyphenolic acids.

Phenolic acids in coffee are mainly esters of quinic acid with different amount of caffeyl groups attached to its different positions. The phenolic acids present in coffee such as chlorogenic acid, caffeic acid, para-coumaric acid and eugenol have been shown to exert cancer preventive activities in animal models. Chlorogenic acid has also been found to inhibit methylazoxymethanol-induced large intestinal tumors in hamster.

Chlorogenic acid, which is the main phenolic acid in coffee, is able to protect the gastric mucosa against irritations, and, therefore, improves the digestibility of foods, beverages and medicaments. The improved digestibility is expressed through a much-reduced systemic acid secretion (such as causes heartburn, etc.), which has been found to be directly dependent on an increased level of chlorogenic acid content in raw green coffee beans.

Normally the natural chlorogenic acid content of green coffee is reduced by approximately 40 to 80% during conventional roasting process. Analysis by the present inventor indicates that green coffee beans which initially contain 8% phenolic acids contain, respectively, 2% phenolic acids when light roasted, 1% when medium roasted, and less than 0.5% when dark roasted. This clearly represents a significant loss of beneficial compounds. Thus, the use of a roasting process which is designed to preserve the polyphenols normally lost through the roasting process will result in a product which has concentrations of phenolic compounds in greater quantities than currently marketed coffee beverages.

The resulting beverage will also be a source of diterpenes which have detoxification properties in humans, as well as other beneficial compounds such as triterpenes.

DETAILED DESCRIPTION OF THE PREFERRED EMBODIMENT

Extensive research by the present inventors produced a finding that post-processing chlorogenic acid content in particular, and total polyphenol content in general, can be substantially enhanced for brewed coffee through a remarkably simple process. The same is true of other brewed beverages the counterpart substrates of which are known to have a significant polyphenolic constituent. Therefore, while the predominant discussion in this specification focuses on coffee, it must be understood that similar results can be obtained through practice of the methods of the present invention in the context of producing beverages from other materials which naturally contain polyphenolic acids (teas, for example).

Both condensed tannin and polyphenolic acids in coffee beans have low water-solubility. According to experiments by the present inventors, under most circumstances, even hot water cannot significantly dissolve coffee polyphenols out of coffee. Something more than water at elevated temperatures applied at some rando0m point in coffee beverage making is required to most significantly enhance the extraction of coffee polyphenols out of coffee beans and powder.

The present inventors have discovered that, if applied in the manner prescribed herein, the remarkably simple process of soaking coffee beans in plain water prior to roasting, and, after roasting, "quenching" the beans with a portion of the pre-soak liquid (the solvent water, plus the polyphenols released into the water) will substantially enhance the post-roasting polyphenol content of coffee beans. This represents yet another significant leap forward in the present inventors' work in optimizing the post-processing polyphenol content of coffee as a means for delivering health-enhancing agents to consumers in a most non-intrusive and cost effective manner.

The process of the present invention, when compared with earlier, related processes developed by the present inventors, not only provides a substantial health benefits potential, but permits such benefits to be realized, and the product which carries the benefits to be distributed and sold, with no market or distribution related impediments or inconveniences. This is true, in part, because, unlike some of the referenced prior processes (the subject of first parent application relating to this continuation application) the process for spiking polyphenolics pursuant to the present invention, at least in the case of coffee, takes place at the commercial, roasting stage, rather than at the retail sales level and is, therefore, completely transparent to the end consumer.

Illustrative examples of processes of the present invention follow. It should be understood, of course, that commercial processing according to the present invention will take place on much larger scales than the illustrative examples provided, with proportional increases in the respective constituents (coffee beans, water, pre-soak liquid used for quenching, etc) for larger batches. The first described example is presently believed to be the optimal process for maximizing polyphenol content in coffee beans and ultimately, therefore, in brewed coffee.

According to the most economical version of the present invention, raw, green coffee beans are "pre-soaked" in water as described in more detail hereafter, and a portion (approximately 10% to 20%) of the same water is later used to quench the same beans immediately after roasting. However, as shown below, variations of the same invention involve pre-soaking green coffee beans, roasting other beans, and quenching the roasted beans with the solution from soaking the first, non-roasted beans. These later methods yield end products of even greater phenolics content.

EXAMPLE 1

Raw green coffee beans are pre-soaked in water for 3 hours at 75 deg C. 1000 grams of green beans soaked in 2000 mls of water. 1000 mls of pre-soak solution (water used for pre-soaking) was retained after beans are removed from water for roasting. Pre-soaked green beans are roasted in a traditional coffee roaster with temperature starting at 350 deg F. and increasing to 430 deg F. over a period of approximately 15–18 minutes.

At the conclusion of the roast, the beans are dropped into a container and immediately quenched with 150 mls of the pre-soak solution. The roasted beans are then ground to a powder and brewed with hot water to produce a coffee beverage.

Chemical analysis showed that the new beverage contains over 20%–65% of the pre-roasted phenolic acid content, specifically representing chlorogenic acid content at 40%–150% (depending on degree of roast—bigger increase with darker roast) over that in traditional roasted coffee of a similar roast color;

EXAMPLE 2

Raw green coffee beans are pre-soaked in water for 3 hours at 80 deg C. 1000 grams of green beans soaked in 2000 mls of water. 1000 mls of pre-soak solution was obtained Pre-soak water is collected for later quenching step. 1400 grams of regular green beans are roasted in a traditional manner. Upon completion of the roast the beans are split into a control and an experimental group and subsequently quenched with either 150 mls of water (control) or 150 mls of the pre-soak solution that has been previously collected from green beans. (experimental). The green beans used to create the pre-soak quenching solution are not the beans that are use in the roasting. The roasted beans are then ground to a powder and brewed with hot water to produce a coffee beverage.

Chemical analysis showed that the new beverage contains over 20%–70% of phenolic acid content, representing a 40%–200% chlorogenic acid content over that of the control of the same roast.

EXAMPLE 3

Raw green coffee beans are pre-soaked in water for 3 hours at 80 deg C. 1000 grams of green beans soaked in 2000 mls of water. 1000 mls of pre-soak solution was obtained. Pre-soak water is collected for later quenching step. A portion of the pre-soak water is collected and freeze dried to be used as a fortifying ingredient in the pre-soak quench. 1400 grams of regular green beans are roasted in a traditional manner. Upon completion of the roast the beans are split into a control and an experimental group and subsequently quenched with either 150 mls of water (control) or 150 mls of the pre-soak which has been fortified with 10 grams of freeze dried pre-soak. All pre-soak solution has been previously collected and/or collected and freeze dried from green beans. (experimental). The green beans used to create the pre-soak quenching solution are not the beans that are use in the roasting. The roasted beans are then ground to a powder and brewed with hot water to produce a coffee beverage.

Chemical analysis showed that the new beverage contains over 120% of phenolic acids, representing approx 250% of chlorogenic acid content of conventionally processed coffee;

The powder from the preceding examples can be sold as coffee powder for brewing or can be brewed and sold as a ready-to-drink coffee beverage. The resulting product can be taken as a food or functional food by a human or other mammal, orally.

CONCLUSIONS

The preceding examples illustrate that a more healthful polyphenol coffee beverage product can be produced by a very simple variation of conventional coffee roasting methods. In addition, an end product which is healthier and not much more costly than existing coffee powders can be produced, and thereby provide a market and economic benefit to vendors. The present method yields a product which is in no way undesirable from an aesthetic standpoint. Thus, there is no reason not to, and every reason to, adopt the present coffee roasting processing methods for the well being of consumers.

The processes of the present invention represent significant departures from conventional production of roasted coffee products, where green beans are simply roasted and may or may not be quenched with water, whereas the end product of the present invention achieves a chemical profile of increased amounts of phenolic acids and other beneficial compounds which is different from existing roasted coffee brews. This new process yields more active, more bioavailable, and larger quantities of phenolic compounds than those found in existing roasted coffee brews.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

We claim:

1. A method for enhancing polyphenolic acid content in post-processing beverage substrates comprising the steps of:
    selecting a measure of beverage substrate known to contain polyphenolic acids;
    immersing said beverage substrate in a pre-soak liquid containing water;
    removing said beverage substrate from said pre-soak liquid and roasting said beverage substrate; and
    quenching said beverage substrate after said roasting with a portion of said pre-soak liquid.

2. The method of claim 1 wherein said beverage substrate is coffee beans.

3. A method for enhancing polyphenolic acid content in post-processing beverage substrates comprising the steps of:
    selecting a first measure of beverage substrate known to contain polyphenolic acids;
    immersing said first measure of beverage substrate in a pre-soak liquid containing water;
    collecting said pre-soak liquid after said immersing;
    roasting a second measure of a beverage substrate; and
    quenching said second measure of beverage substrate after said roasting with a portion of said pre-soak liquid.

4. The method of claim 1 wherein said first beverage substrate comprises coffee beans.

5. The method of claim 1 wherein said second beverage substrate comprises coffee beans.

6. The method of claim 1 wherein said first beverage substrate and said second beverage substrate comprise coffee beans.

7. The method of claim 1 wherein said first beverage substrate consists essentially of coffee beans.

8. The method of claim 1 wherein said second beverage substrate consists essentially of coffee beans.

9. The method of claim 1 wherein said first beverage substrate and said second beverage substrate consist essentially of coffee beans.

* * * * *